(12) United States Patent
Rothermel

(10) Patent No.: US 10,953,186 B2
(45) Date of Patent: Mar. 23, 2021

(54) FLUID COUPLING CONDUIT FOR A PATIENT INTERFACE DEVICE

(71) Applicant: KONINKLIJKE PHILIPS N.V., Eindhoven (NL)

(72) Inventor: Justin Edward Rothermel, Monroeville, PA (US)

(73) Assignee: Koninklijke Philips N.V., Eindhoven (NL)

( * ) Notice: Subject to any disclaimer, the term of this patent is extended or adjusted under 35 U.S.C. 154(b) by 417 days.

(21) Appl. No.: 15/329,817

(22) PCT Filed: Jul. 31, 2015

(86) PCT No.: PCT/IB2015/055807
§ 371 (c)(1),
(2) Date: Jan. 27, 2017

(87) PCT Pub. No.: WO2016/016856
PCT Pub. Date: Feb. 4, 2016

(65) Prior Publication Data
US 2018/0207387 A1 Jul. 26, 2018

(51) Int. Cl.
*A61M 16/08* (2006.01)
*A61M 16/06* (2006.01)

(52) U.S. Cl.
CPC ........ *A61M 16/0816* (2013.01); *A61M 16/06* (2013.01); *A61M 2205/42* (2013.01)

(58) Field of Classification Search
CPC .. A61M 16/0816; A61M 16/06; A61M 16/00; A61M 16/0833; A61M 16/0825; A61M 16/20; A61M 16/208; A61M 16/209; A61M 16/0875; A61M 16/0883; A61M 2205/42; A61M 2016/0661
USPC ............ 128/206.24, 206.26, 200.24, 204.18, 128/205.25, 206.21, 206.28; 137/115.12, 137/855; 138/39, 113, 92, 94
See application file for complete search history.

(56) References Cited

U.S. PATENT DOCUMENTS

| | | | |
|---|---|---|---|
| 9,242,060 B2 * | 1/2016 | Fu ......................... | A61M 16/06 |
| 2001/0035004 A1 | 11/2001 | Balzer | |
| 2003/0005931 A1 * | 1/2003 | D. Jaffre ............... | A61M 16/08 |
| | | | 128/204.18 |
| 2003/0213227 A1 | 11/2003 | Balzer | |

(Continued)

FOREIGN PATENT DOCUMENTS

| | | |
|---|---|---|
| CN | 103906546 A | 7/2014 |
| EP | 2027880 A1 | 2/2009 |

(Continued)

*Primary Examiner* — Kendra D Carter
*Assistant Examiner* — Benjamin M. Kusiak
(74) *Attorney, Agent, or Firm* — Michael W. Haas

(57) ABSTRACT

A fluid coupling conduit is for a patient interface device. The fluid coupling conduit includes a body including: an inlet end structured to receive a flow of breathing gas, an outlet end fluidly coupled to the inlet end, and a middle portion disposed between the inlet end and the outlet end, the middle portion including a rim defining a relief aperture provided in an aperture plane. The fluid coupling conduit further includes a blocking member substantially disposed in the relief aperture, a number of openings being formed between the blocking member and the rim. The rim includes a number of protrusions extending transversely to the aperture plane.

14 Claims, 9 Drawing Sheets

(56) References Cited

U.S. PATENT DOCUMENTS

| | | | |
|---|---|---|---|
| 2006/0266365 A1 | 11/2006 | Stallard | |
| 2009/0050156 A1 | 2/2009 | Ng | |
| 2009/0107506 A1* | 4/2009 | Collazo | A61M 16/06 128/206.21 |
| 2010/0258133 A1* | 10/2010 | Todd | A61M 15/009 128/207.12 |
| 2011/0240030 A1* | 10/2011 | Ho | A61M 16/06 128/206.21 |
| 2012/0266884 A1* | 10/2012 | Ho | A61M 16/06 128/205.25 |
| 2013/0327336 A1* | 12/2013 | Burnham | A61M 16/0816 128/206.21 |
| 2014/0305433 A1* | 10/2014 | Rothermel | A61M 16/06 128/202.27 |

FOREIGN PATENT DOCUMENTS

| | | | | |
|---|---|---|---|---|
| WO | WO2010067237 A2 | 6/2010 | | |
| WO | WO2012052906 A1 | 4/2012 | | |
| WO | 2012109704 A1 | 8/2012 | | |
| WO | WO2013064931 A1 | 5/2013 | | |
| WO | WO-2015092589 A1 * | 6/2015 | ......... | A61M 16/208 |
| WO | WO2015092589 A1 | 6/2015 | | |

* cited by examiner

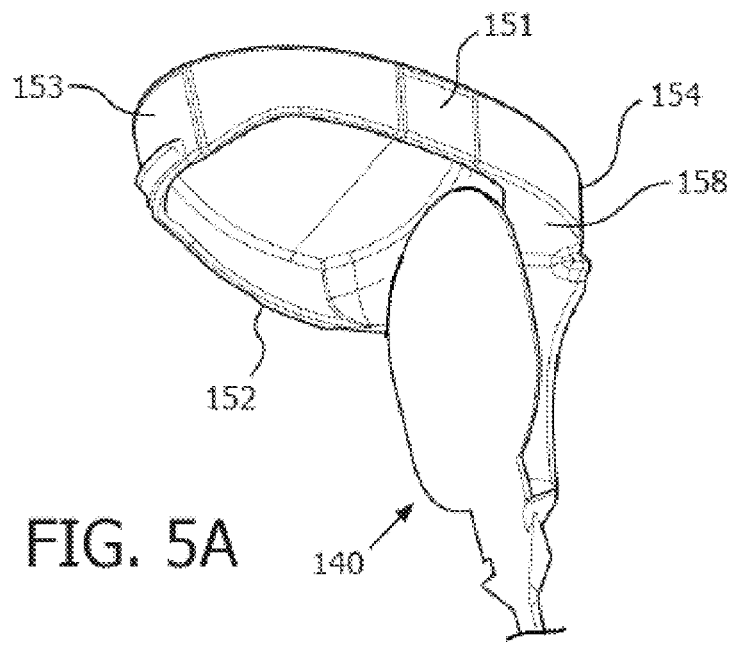
FIG. 5A
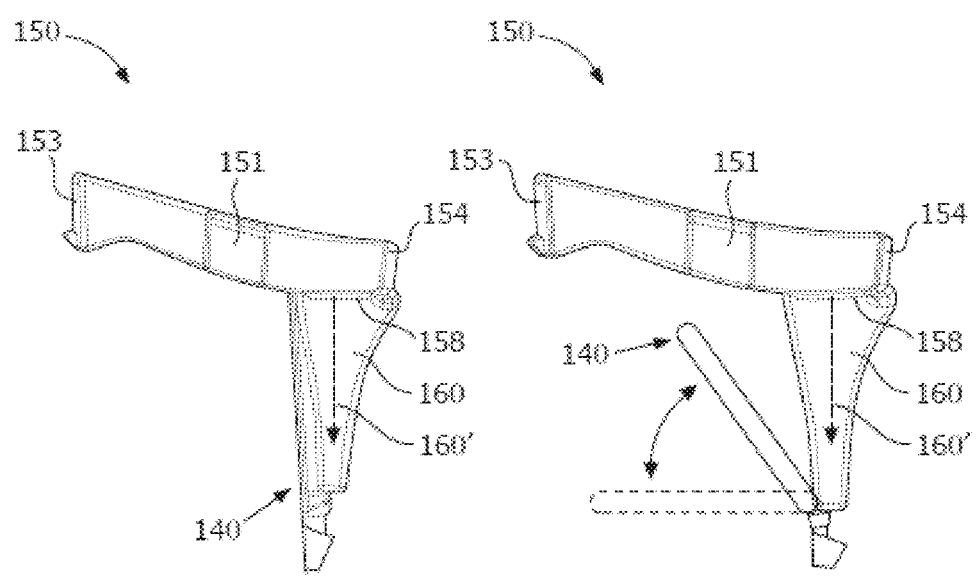
FIG. 5B
FIG. 5C

FLUID COUPLING CONDUIT FOR A PATIENT INTERFACE DEVICE

CROSS-REFERENCE TO RELATED APPLICATIONS

This patent application claims the priority benefit under 35 U.S.C. 371 of international patent application no. PCT/IB2015/055807, filed Jul. 31, 2015, which claims the priority benefit under 35 U.S.C. § 119(e) of U.S. Provisional Application No. 62/031,483 filed on Jul. 31, 2014, the contents of which are herein incorporated by reference.

BACKGROUND OF THE INVENTION

1. Field of the Invention

The present invention relates to non-invasive ventilation and pressure support systems wherein a patient interface device is used to deliver a flow of breathing gas to a patient, and in particular to a fluid coupling conduit, such as an elbow conduit, for such a patient interface device that includes a mechanism for reducing noise caused by patient exhaust.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver positive airway pressure (PAP) therapy to treat certain medical disorders, the most notable of which is obstructive sleep apnea (OSA). Known PAP therapies include continuous positive airway pressure (CPAP), wherein a constant positive pressure is provided to the airway of the patient in order to splint open the patient's airway, and variable airway pressure, wherein the pressure provided to the airway of the patient is varied with the patient's respiratory cycle. Such therapies are typically provided to the patient at night while the patient is sleeping.

Non-invasive ventilation and pressure support therapies as just described involve the placement of a patient interface device including a mask component having a soft, flexible cushion on the face of a patient. The mask component may be, without limitation, a nasal mask that covers the patient's nose, a nasal cushion having nasal prongs that are received within the patient's nares, a nasal/oral mask that covers the nose and mouth, or a full face mask that covers the patient's face. Such patient interface devices may also employ other patient contacting components, such as forehead supports, cheek pads and chin pads. The patient interface device is connected to a gas delivery hose and interfaces the ventilator or pressure support device with the airway of the patient, so that a flow of breathing gas can be delivered from the pressure/flow generating device to the airway of the patient. It is known to maintain such devices on the face of a wearer by a headgear having one or more straps adapted to fit over/around the patient's head.

For patient interface devices used in, for example, the treatment of OSA, a key engineering challenge is to balance exhaust flow and exhaust noise. A certain amount of exhaust flow is required for all such patient interface devices to properly expel as much $CO_2$ as possible. The amount of exhaust flow currently required to expel the proper amount of $CO_2$ also makes the patient interface devices somewhat noisy. This noise could disturb a patient or bed partner, sometimes to the point where he or she will not be able to fall asleep or will be woken up inadvertently. Thus, there is room for improvement in fluid coupling conduits and in patient interface devices employing the same.

SUMMARY OF THE INVENTION

As one aspect of the disclosed concept, a fluid coupling conduit for a patient interface device is provided. The fluid coupling conduit comprises: a body comprising: an inlet end structured to receive a flow of breathing gas, an outlet end fluidly coupled to the inlet end, and a middle portion disposed between the inlet end and the outlet end, the middle portion comprising a rim defining a relief aperture provided in an aperture plane. The fluid coupling conduit further comprises a blocking member substantially disposed in the relief aperture. A number of openings are formed between the blocking member and the rim. The rim comprises a number of protrusions extending transversely to the aperture plane.

As another aspect of the disclosed concept, a patient interface device is provided. The patient interface device comprises: a cushion; a frame, the cushion being coupled to the frame, the frame having an orifice in fluid communication with the cushion; and a fluid coupling conduit comprising: a body comprising: an inlet end structured to receive a flow of breathing gas, an outlet end fluidly coupled to the inlet end, and a middle portion disposed between the inlet end and the outlet end, the middle portion comprising a rim defining a relief aperture provided in an aperture plane. The fluid coupling conduit further comprises a blocking member substantially disposed in the relief aperture, a number of openings being formed between the blocking member and the rim. The rim comprises a number of protrusions extending transversely to the aperture plane. The outlet end is structured to be fluidly coupled to the orifice of the frame to deliver the flow of breathing gas to the cushion.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

BRIEF DESCRIPTION OF THE DRAWINGS

FIGS. 5A through 5C are different views of a flapper component and the blocking member for the fluid coupling conduit of FIGS. 2A and 2B;

DETAILED DESCRIPTION OF THE EXEMPLARY EMBODIMENTS

Figure 1A:
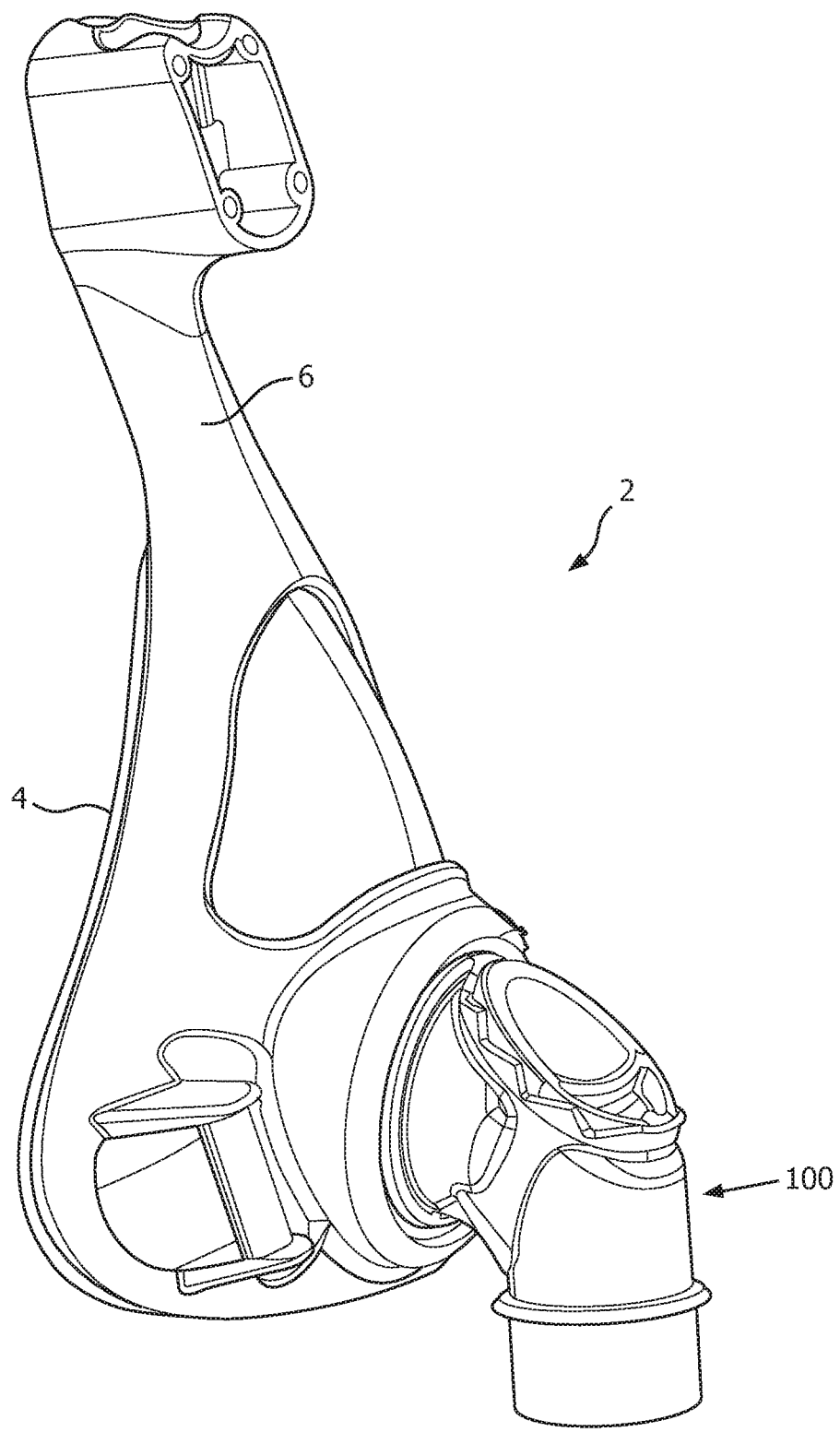
FIGS. 1A and 1B are front isometric and exploded front isometric views, respectively, of a patient interface device according to one exemplary embodiment of the present invention.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein. As employed, herein, the statement that two or more parts or components are "coupled" together shall mean that the parts are joined or operate together either directly or through one or more intermediate parts or components.

As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Figure 1B:
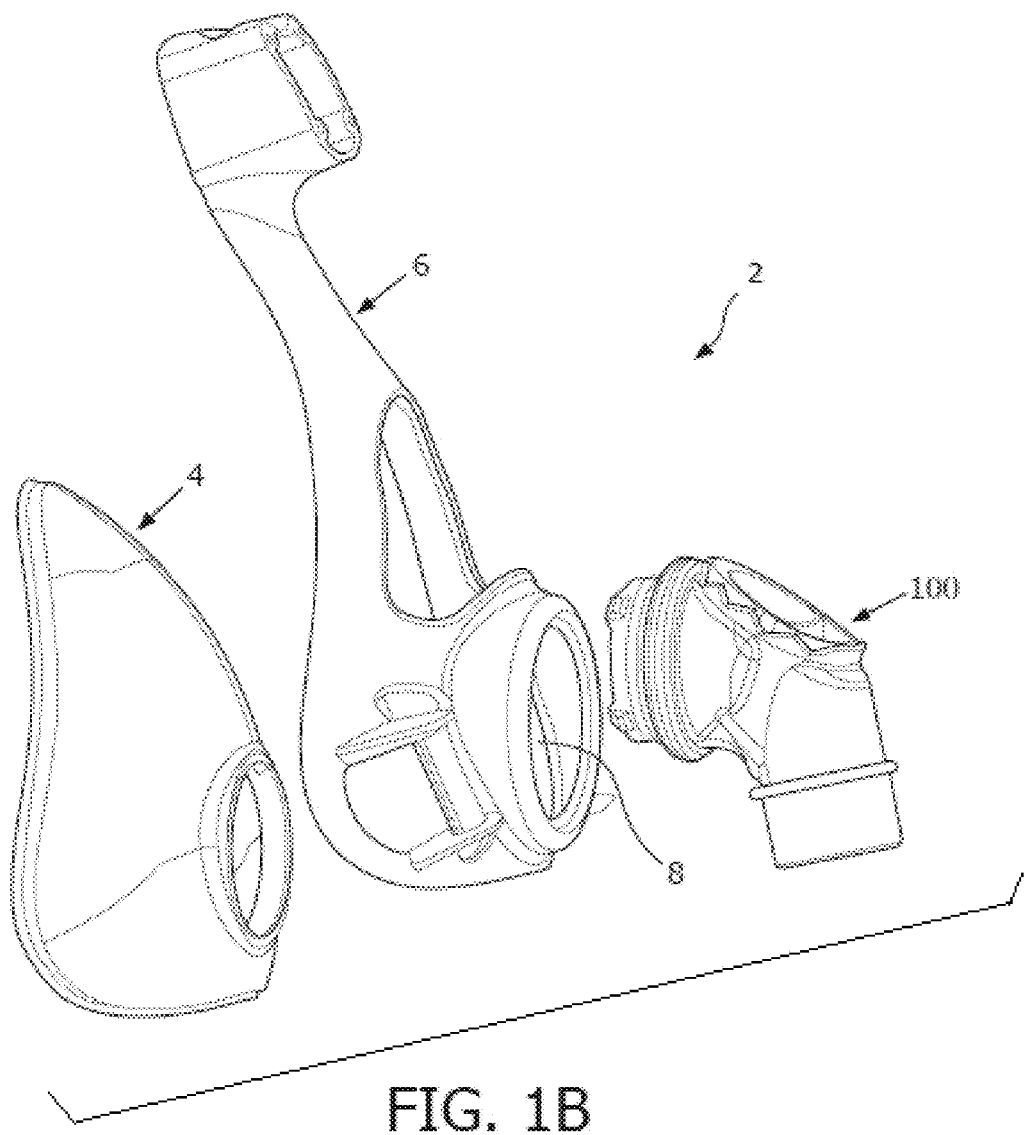

FIG. 1A is a front isometric view and FIG. 1B is an exploded isometric view of a patient interface device 2 that includes a cushion 4, a frame 6 coupled to cushion 4, and a fluid coupling conduit 100, according to one exemplary embodiment of the present invention. Fluid coupling conduit 100 is structured to be coupled to a suitable hose, which in turn is coupled to a suitable pressure generating device, which may include, without limitation, a constant pressure support device (such as a continuous positive airway pressure device, or CPAP device), a variable pressure device (e.g., BiPAP®, Bi-Flex®, or C-Flex™ devices manufactured and distributed by Philips Respironics of Murrysville, Pa.), an auto-titration pressure support device, or a ventilator.

In the illustrated embodiment, cushion 4 is defined from a unitary piece of soft, flexible, cushiony, elastomeric material, such as, without limitation, silicone, an appropriately soft thermoplastic elastomer, a closed cell foam, or any combination of such materials. Frame 6 is made of a rigid or semi-rigid material, such as, without limitation, an injection molded thermoplastic or silicone, and includes an orifice 8 (FIG. 1B) to which fluid coupling conduit 100 is coupled. Orifice 8 is structured to be in fluid communication with cushion 4 and fluid coupling conduit 100. Fluid coupling conduit 100 is described in detail below in connection with FIGS. 2A-5C.

Figure 2A:
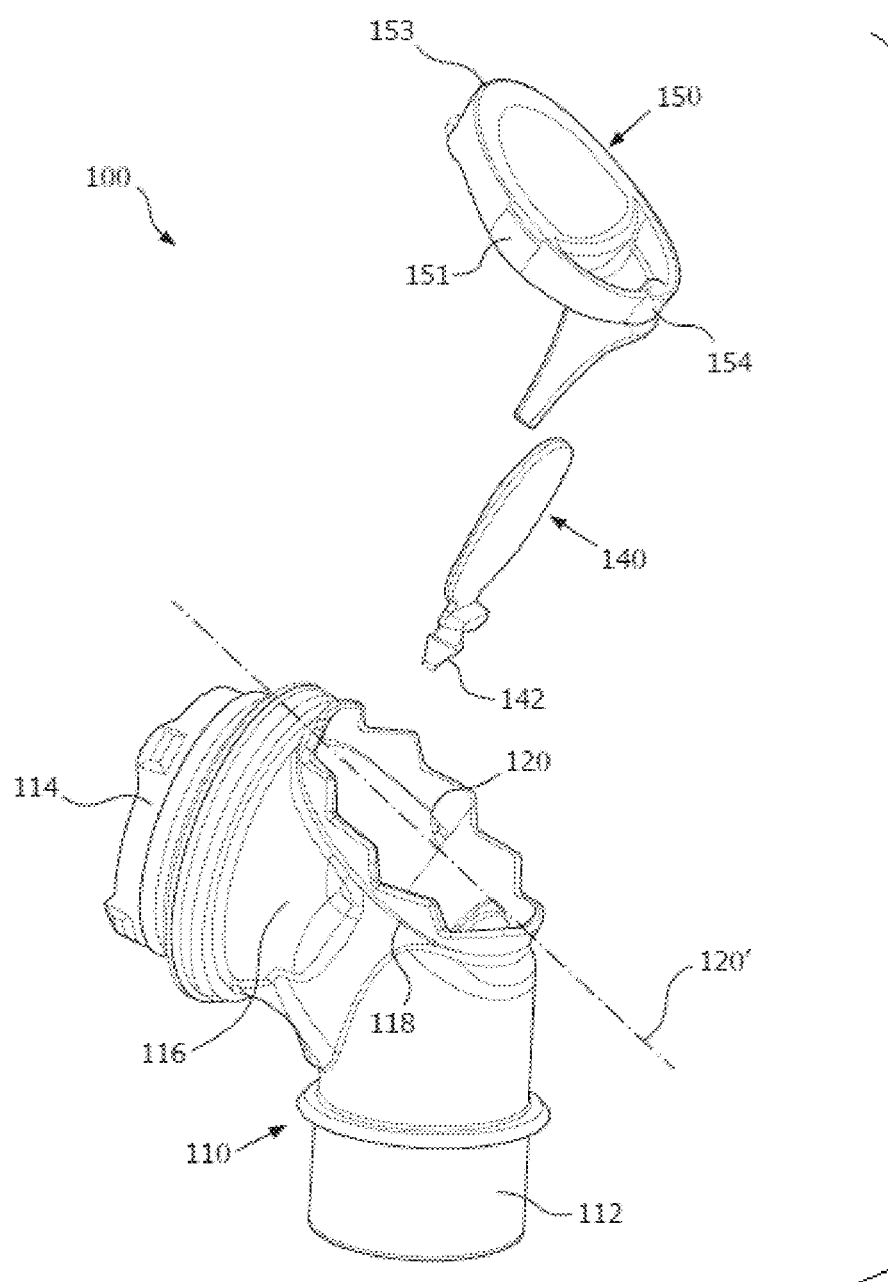
FIGS. 2A and 2B are exploded front isometric and top views, respectively, of a fluid coupling conduit for the patient interface device of FIGS. 1A and 1B.
Figure 2B:
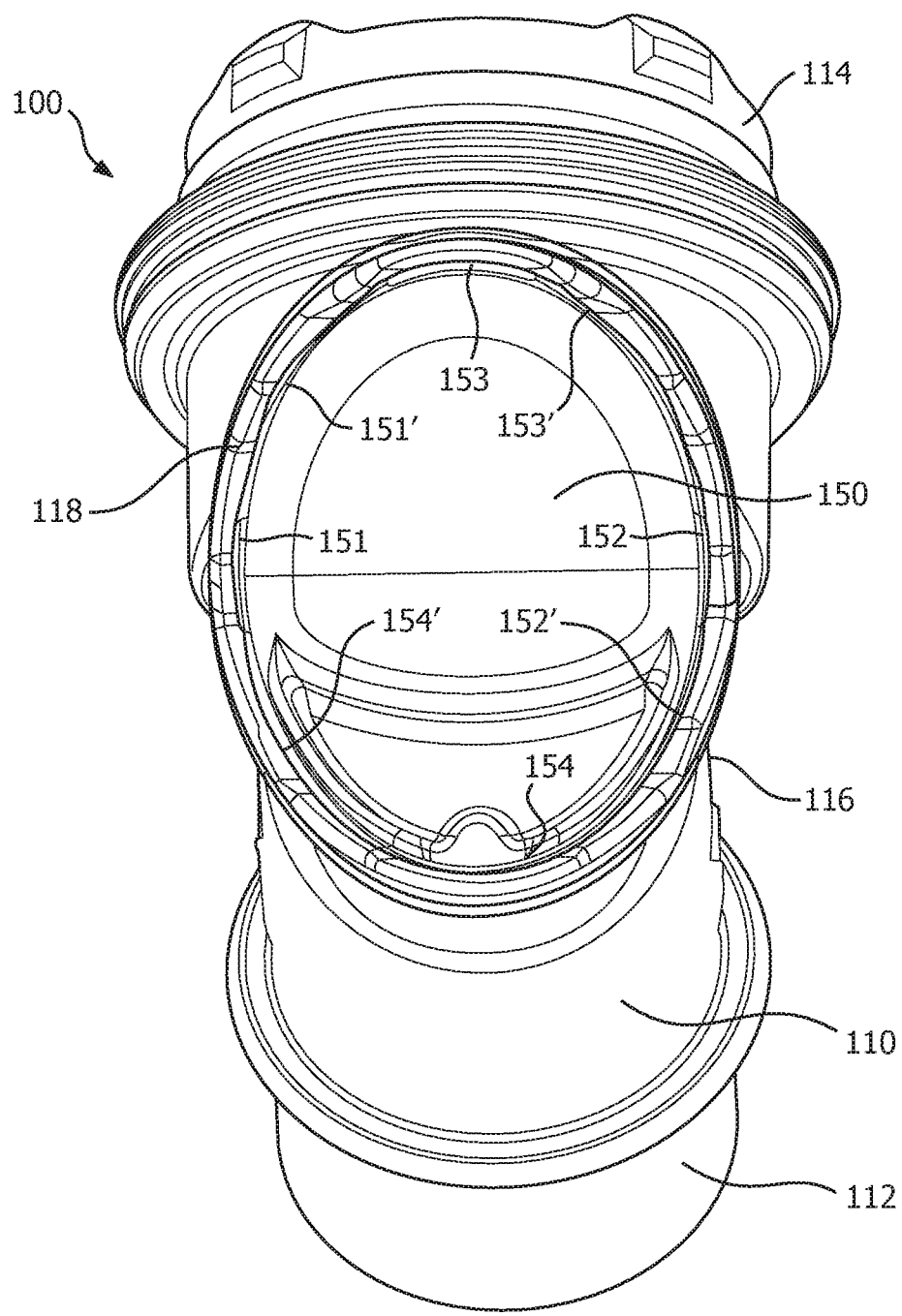

FIG. 2A is an exploded view and FIG. 2B is a top view of fluid coupling conduit 100. As seen, fluid coupling conduit 100 includes a body 110, a flapper component 140 (FIG. 2A) structured to be located in body 110, and a blocking member 150 structured to partially extend into body 110. Body 110 includes an inlet end 112, an outlet end 114, and a middle portion 116 located between inlet end 112 and outlet end 114. Inlet end 112 is structured to be fluidly coupled to a hose in order to receive a flow of breathing gas, as described hereinabove. Additionally, outlet end 114 is fluidly coupled to inlet end 112 and structured to be coupled to orifice 8 of frame 6 (FIG. 1A and FIG. 1B) in order to deliver breathing gas to cushion 4. Middle portion 116 includes a rim 118 defining a relief aperture 120 located in an aperture plane that includes line 120'. Blocking member 150 is substantially located within relief aperture 120 and is preferably coupled to body 110 by a snap-fit mechanism. However, it is within the scope of the disclosed concept for blocking member 150 to be coupled to body 110 by any known or suitable alternative mechanism (e.g., without limitation, being ultrasonically welded or glued to body 110).

Referring to FIG. 2B, blocking member 150 includes a number of outwardly extending projections 151,152,153, 154. Projection 151 is opposite projection 152 and projection 153 is opposite projection 154. Furthermore, each of projections 151,152 is located between projections 153,154. Projections 151,152,153,154 are structured to engage rim 118 of body 110. In this manner, a number of openings 151',152',153',154' are formed between blocking member 150 and rim 118 of body 110. During normal use of patient interface device 2 (FIG. 1A and FIG. 1B), as will be discussed in greater detail hereinbelow, exhaust air from a patient is structured to be expelled through openings 151', 152',153',154'.

Figure 3A:
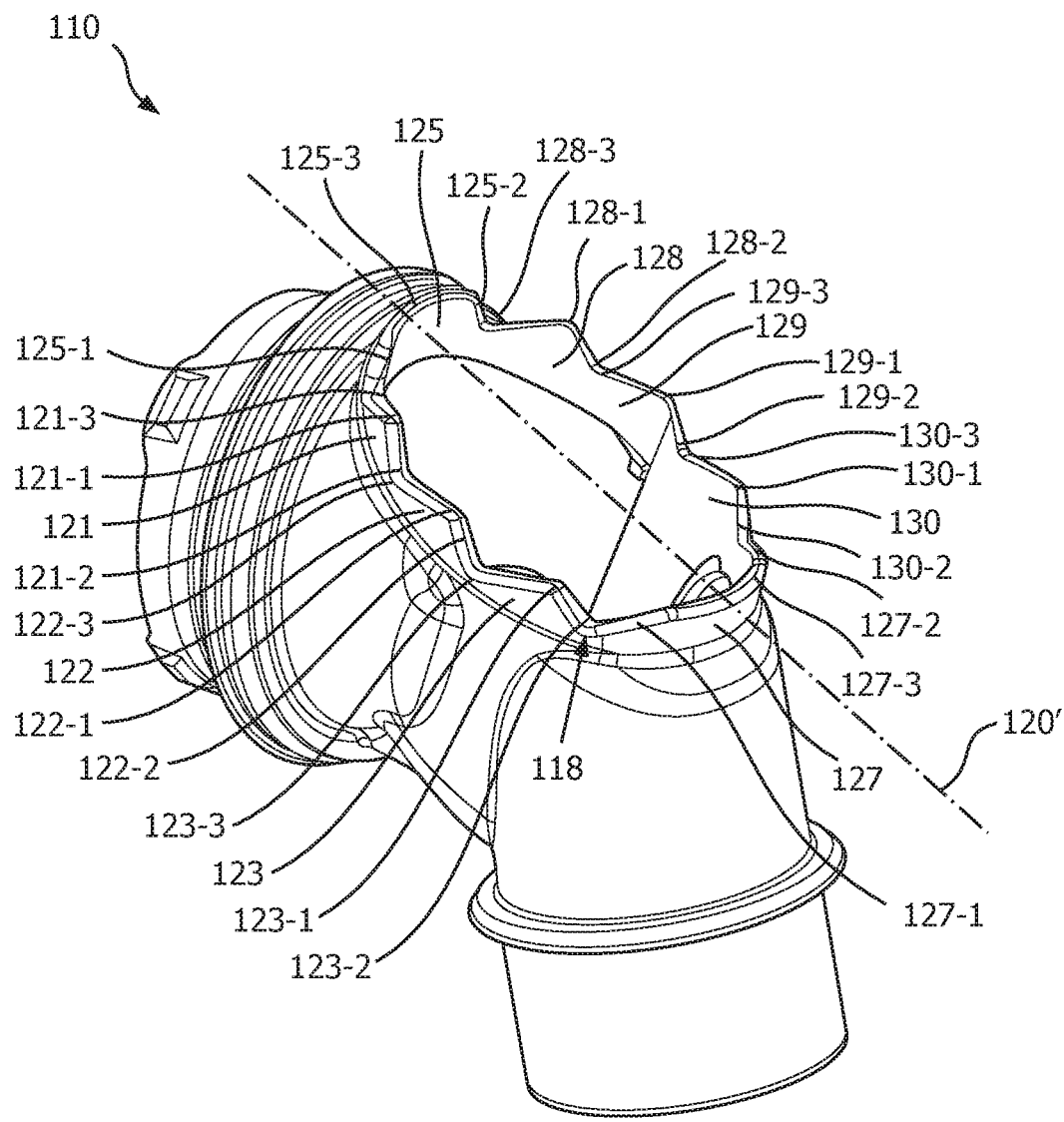
FIGS. 3A through 3C are different views of a body for the fluid coupling conduit of FIGS. 2A and 2B.
Figure 3B:
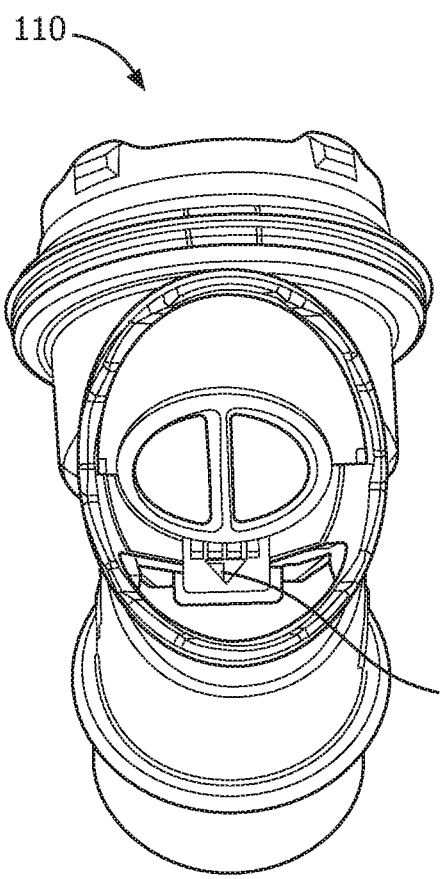
Figure 3C:
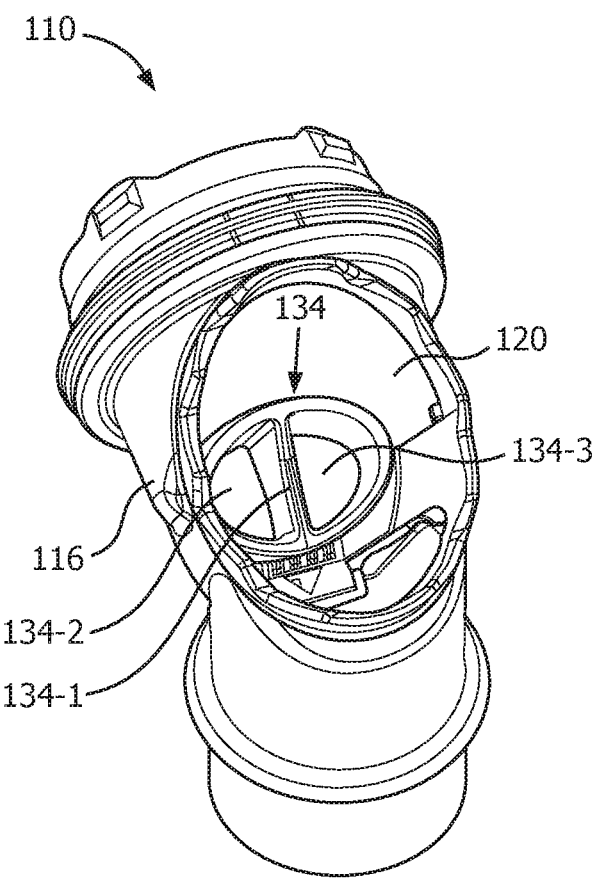

FIGS. 3A through 3C are different views of body 110. Referring to FIG. 3A, rim 118 includes a number of protrusions 121,122,123,125,127,128,129,130 extending transversely to aperture plane 120' (FIG. 2A). Furthermore, as seen in the illustrated non-limiting embodiment, rim 118 is serrated in a manner wherein each of the protrusions 121, 122,123,128,129,130 is a V-shaped member including peaks 121-1,122-1,123-1,128-1,129-1,130-1 and corresponding base regions 121-2,121-3,122-2,122-3,123-2,-123-3,128-2, 128-3,129-2,129-3,130-2,130-3 which extend from rim 118.

Furthermore, protrusions 125,127 are support protrusions which advantageously simplify manufacturing of body 110 (e.g., without limitation, simplify injection molding). Support protrusions 125,127 each include a pair of spaced apart outwardly extending edges 125-1,125-2,127-1,127-2 and a distal edge 125-3,127-3 connecting edges 125-1,127-1 to corresponding edges 125-2,127-2. As seen, V-shaped members 121,122,123,128,129,130 are located on opposing sides of rim 118 between support protrusions 125,127. While the disclosed concept has been described in association with support protrusions 125,127, it will be appreciated that a rim (not shown) may include V-shaped members extending along the entire perimeter. Additionally, a rim may include protrusions with alternative shapes and/or configurations, as will be discussed in greater detail hereinbelow.

Referring to FIG. 3B, body 110 has a generally triangular-shaped through hole 132. Furthermore, flapper component 140 (FIG. 2A) includes a base portion 142 having a larger cross-sectional area than through hole 132. During assembly, because flapper component is preferably made of a soft elastomeric material, flapper component 140 is able to be pulled through hole 132. Additionally, because base portion 142 has a larger cross-sectional area than through hole 132, flapper component 140 is advantageously able to be secured within fluid coupling conduit 100.

As seen in FIG. 3C, middle portion 116 of body 110 further includes an atmospheric port 134, the function of which will be discussed hereinbelow. Atmospheric port 134 is located opposite and distal from relief aperture 120 and includes a dividing wall 134-1 that separates a pair of opposing side portions 134-2, 134-3.

Figure 4A:
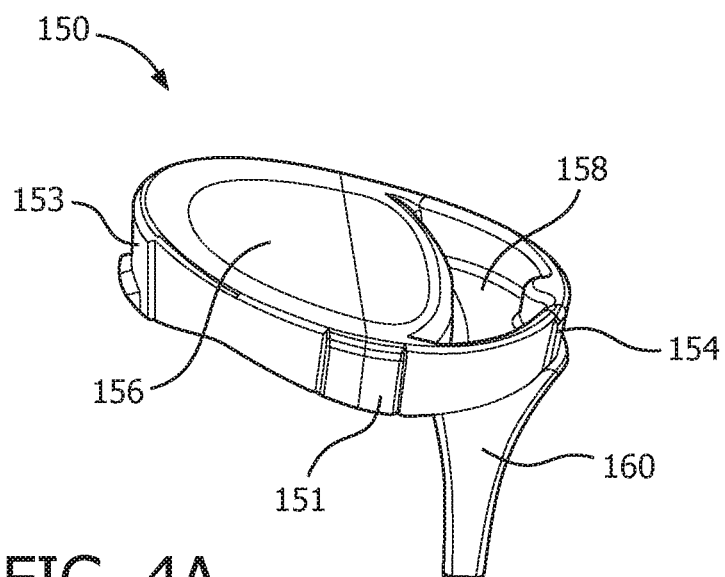
FIGS. 4A through 4C are different views of a blocking member for the fluid coupling conduit of FIGS. 2A and 2B.
Figure 4B:
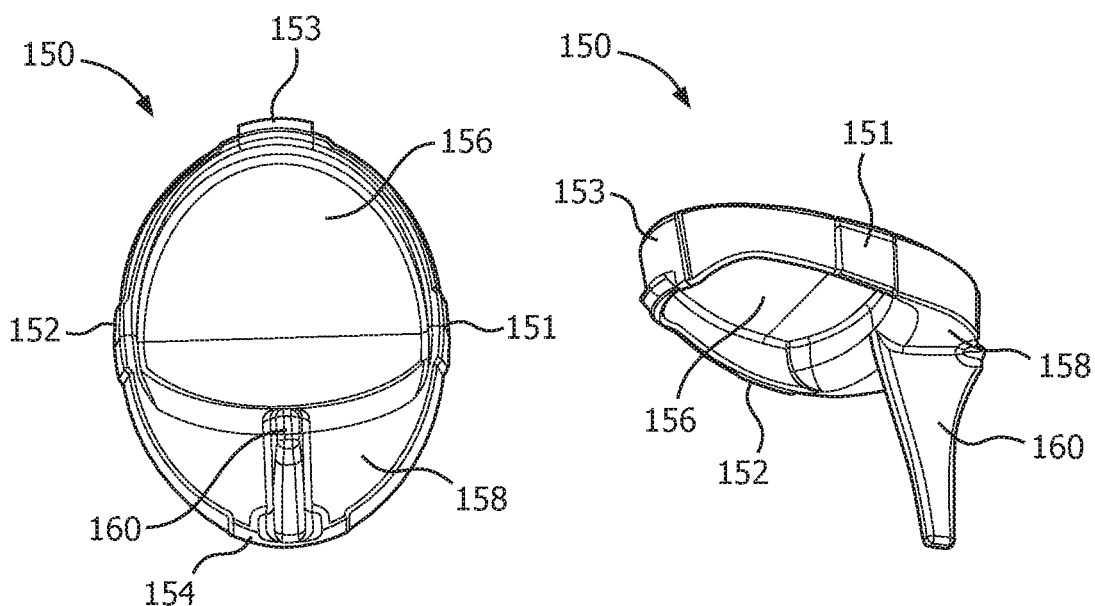
Figure 4C:
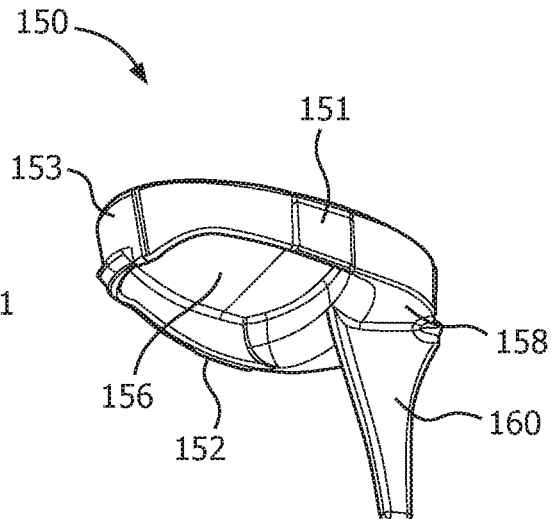

FIGS. 4A-4C show different views of blocking member 150. As seen in FIG. 4A, blocking member 150 includes a generally planar portion 156, a recessed portion 158 adjacent planar portion 156, and a rib 160 extending from recessed portion 158. It will however be appreciated that a blocking member (not shown) having any known or suitable alternative shape and/or configuration (not shown) may be employed to perform the desired function of substantially blocking relief aperture 120 while allowing breathing gas to escape through a number of openings. Recessed portion 158 generally functions to accommodate rib 160, which extends from recessed portion 158 inwards with respect to body 110 (FIGS. 2A-3C).

FIGS. 5A-5C show different views of flapper component 140 assembled with blocking member 150. As seen in FIGS. 5B and 5C, rib 160 extends from recessed portion 158 in a direction 160'. Flapper component 140 is structured to move between an open position (FIG. 5B) and a closed position (see generally FIG. 5C), depending on whether a pressure generating device is turned on or off. When flapper component 140 is in the open position (FIG. 5B), flapper component 140 is generally parallel with direction 160'. Furthermore, as seen in FIG. 5A, when flapper component 140 is in the open position, flapper component 140 engages recessed portion 158. Referring to FIG. 5C, responsive to flapper component 140 moving from the open position toward the closed position, flapper component 140 pivots with respect to rib 160 and moves away from recessed portion 158.

During standard operation, such as when the pressure generating device is turned on, breathing gas is structured to enter inlet end 112 and force flapper component 140 to the closed position (FIG. 5C), in which it substantially covers atmospheric port 134. In this position, dividing wall 134-1 advantageously prevents flapper component 140 from being pulled through atmospheric port 134. As the patient exhales, breathing gas passes through orifice 8 of frame 6 as well as corresponding outlet end 114 of body 110. Because atmospheric port 134 is covered by flapper component 140, the exhaled breathing gas is forced through openings 151',152', 153',154' between blocking member 150 and rim 118.

As the breathing gas passes through openings 151',152', 153',154', protrusions 121,122,123,125,127,128,129,130 advantageously enable the breathing gas to diffuse as it exits fluid coupling conduit 100. More specifically, peaks 121-1, 122-1,123-1,128-1,129-1,130-1 are spaced a farther distance from rim 118 than base regions 121-2,121-3,122-2,122-3, 123-2,-123-3,128-2,128-3,129-2,129-3,130-2,130-3. In this manner, breathing gas that passes from rim 118 to peaks 121-1,122-1,123-1,128-1,129-1,130-1 has a farther distance to travel and thus gains momentum and exits fluid coupling conduit 100 at a higher velocity than breathing gas passing from rim 118 to base regions 121-2,121-3,122-2,122-3,123-2,-123-3,128-2,128-3,129-2,129-3,130-2,130-3. As the higher velocity breathing gas and the lower velocity breathing gas exit fluid coupling conduit 100, they pull gas from the surrounding atmosphere with them and also mix with each other. As a result, the overall movement of breathing gas exiting fluid coupling conduit 100 is advantageously lessened. This corresponds to noise associated with exhaust being significantly attenuated. Furthermore, the projected force and/or distance of exhausted gas may be reduced.

During non-standard conditions, such as during a power outage or other situation where the pressure generating device is turned off, flapper component 140 moves from the closed position to the open position (FIG. 5B) and the patient is advantageously able to breathe through atmospheric port 134.

Figure 6:
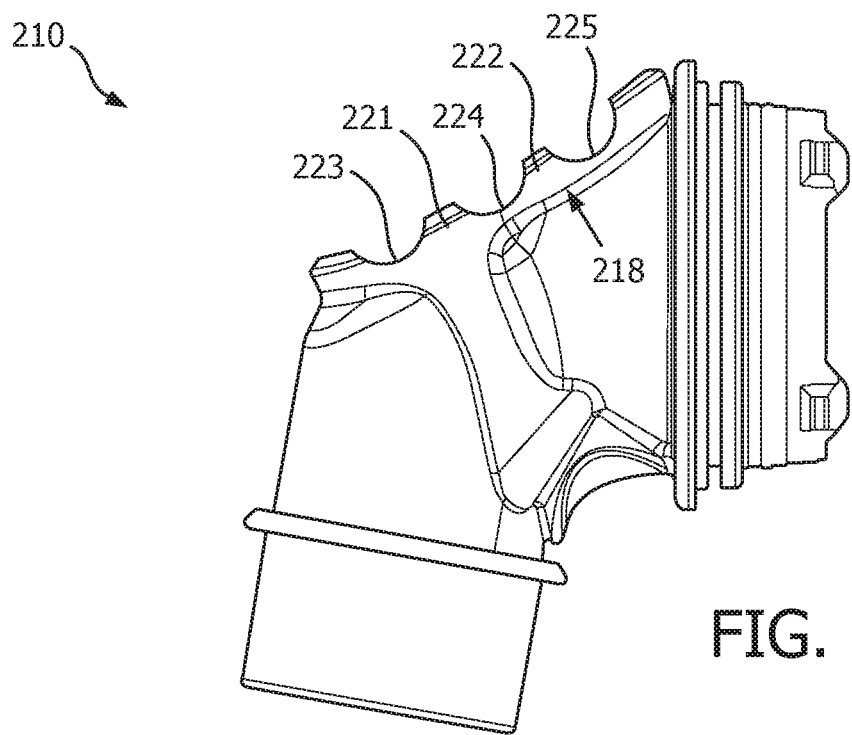
FIG. 6 is an elevation view of a body in accordance with an alternative exemplary embodiment of the disclosed concept.
Figure 7:
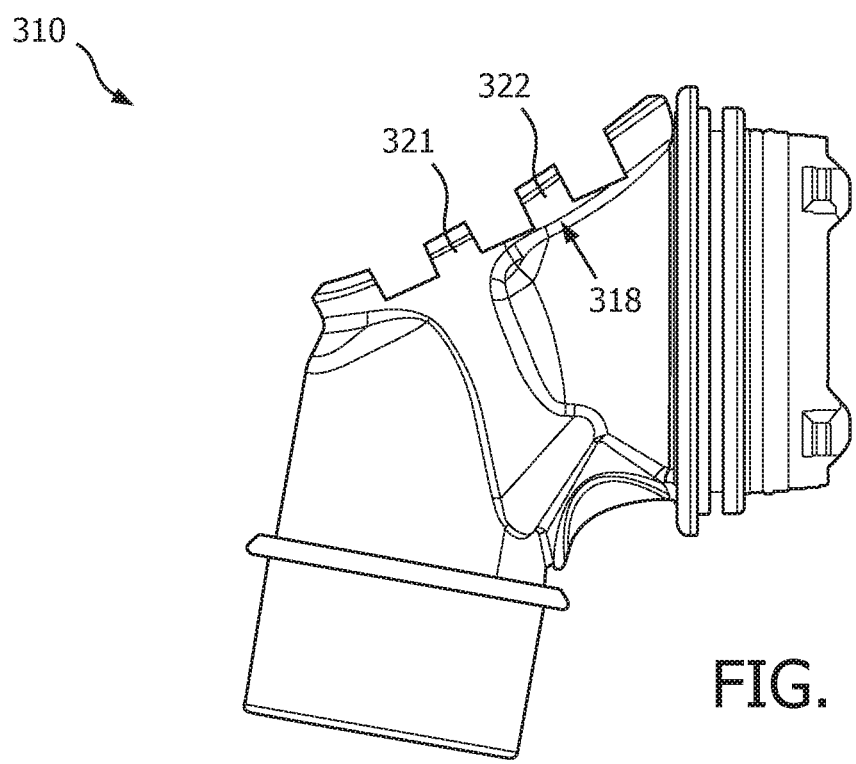
FIG. 7 is an elevation view of a body in accordance with a further alternative exemplary embodiment of the disclosed concept.

FIG. 6 is an elevation view of a body 210 and FIG. 7 is an elevation view of a body 310. As seen in FIG. 6, body 210 includes a rim 218 having a number of protrusions 221,222. Protrusions 221,222 are members that are bordered on each side by a corresponding U-shaped portion 223,224,225. Referring to FIG. 7, body 310 includes a rim 318 having a number of protrusions 321,322 that are generally rectangular-shaped members. Protrusions 221,222,321,322 function substantially similarly as protrusions 121,122,123,125,127, 128,129,130 of body 110. By employing body 210 or body 310 in patient interface device 2 instead of body 110, noise associated with exhaust, and projected force and/or distance of exhausted gas are likewise advantageously reduced. Thus, it can further be understood that protrusions in association with the disclosed concept are not limited to a specific shape and/or configuration.

Accordingly, it will be appreciated that the disclosed concept provides for an improved (e.g., without limitation, slower and less noisy) patient interface device 2 and fluid coupling conduit 100 therefor, which among other benefits, provides for significant diffusion of breathing gas expelled by a patient using a pressure generating device. Additionally, manufacturing is significantly simplified and thus less expensive by employing fewer components with fewer structural features.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A fluid coupling conduit for a patient interface device, comprising:
    (a) a body comprising:
        (i) an inlet end structured to receive a flow of breathing gas,
        (ii) an outlet end fluidly coupled to the inlet end, and
        (iii) a middle portion disposed between the inlet end and the outlet end, the middle portion comprising a rim defining a relief aperture provided in an aperture plane; and
    (b) a blocking member substantially disposed in the relief aperture, wherein the blocking member comprises a plurality of projections, each structured to engage the rim, the rim comprises a number of protrusions extending transversely to the aperture plane, and the plurality of projections form a respective number of openings between the blocking member and the rim,
    wherein the rim is contoured in a manner such that a plurality of the number of protrusions comprise a V-shaped member, and wherein the number of protrusions further comprise a pair of opposing support protrusions, each of the support protrusions comprising a pair of spaced apart outwardly extending edges and a distal edge connecting the outwardly extending edges, and the V-shaped members are disposed on opposing sides of the rim between the support protrusions.

2. The fluid coupling conduit of claim 1, wherein the blocking member further comprises: a rib extending inwards with respect to the body.

3. The fluid coupling conduit of claim 2, wherein the blocking member has a generally planar portion and a recessed portion adjacent the planar portion and the rib extends inwards from the recessed portion.

4. The fluid coupling conduit of claim 3, wherein the rib extends inwards in a direction from the recessed portion, and the fluid coupling conduit further comprises:
   a flapper component disposed on the body, wherein the flapper component is structured to move between an open position and a closed position, in the open position the flapper component is generally parallel with the direction from the recessed portion, and the flapper component pivots with respect to the rib when moving from the open position to the closed position.

5. The fluid coupling conduit of claim 1, wherein the blocking member has a generally planar portion and a recessed portion adjacent the planar portion and the fluid coupling conduit further comprises:
   a flapper component disposed on the body, wherein the flapper component is structured to move between an open position and a closed position, in the open position, the flapper component engages the recessed portion, and the flapper component moves away from the recessed portion when moving from the open position to the closed position.

6. The fluid coupling conduit of claim 1, wherein the blocking member is coupled to the body by a snap-fit mechanism.

7. The fluid coupling conduit of claim 1, wherein the middle portion of the body has an atmospheric port disposed opposite and distal from the relief aperture.

8. A patient interface device, comprising:
   (a) a cushion;
   (b) a frame, the cushion being coupled to the frame, the frame having an orifice in fluid communication with the cushion; and
   (c) a fluid coupling conduit comprising:
      (i) a body comprising:
         (1) an inlet end structured to receive a flow of breathing gas,
         (2) an outlet end fluidly coupled to the inlet end, and
         (3) a middle portion disposed between the inlet end and the outlet end, the middle portion comprising a rim defining a relief aperture provided in an aperture plane, and
      (ii) a blocking member substantially disposed in the relief aperture, wherein the blocking member comprises a plurality of projections, each structured to engage the rim, the rim comprises a number of protrusions extending transversely to the aperture plane, the plurality of projections form a respective number of openings between the blocking member and the rim, and the outlet end is structured to be fluidly coupled to the orifice of the frame to deliver the flow of breathing gas to the cushion,
   wherein the rim is contoured in a manner such that a plurality of the number of protrusions comprise a V-shaped member, and wherein the number of protrusions further comprise a pair of opposing support protrusions, each of the support protrusions comprising a pair of spaced apart outwardly extending edges and a distal edge connecting the outwardly extending edges, and the V-shaped members are disposed on opposing sides of the rim between the support protrusions.

9. The patient interface device of claim 8, wherein and the plurality of projections comprises:
   a first projection;
   a second projection;
   a third projection; and
   a fourth projection; wherein the first projection is opposite the second projection, the third projection is opposite the fourth projection, and each of the first projection and the second projection is disposed between the third projection and the fourth projection.

10. The patient interface device of claim 8, wherein the blocking member comprises: rib extending inwards with respect to the body, the blocking member has a generally planar portion and a recessed portion adjacent the planar portion, and the rib extends inwards from the recessed portion.

11. The patient interface device of claim 10, wherein the rib extends inwards in a direction from the recessed portion, the fluid coupling conduit further comprises: a flapper component disposed on the body, wherein the flapper component is structured to move between an open position and a closed position, in the open position the flapper component is generally parallel with the direction from the recessed portion, and the flapper component pivots with respect to the rib when moving from the open position to the closed position.

12. The patient interface device of claim 8, wherein the blocking member has a generally planar portion and a recessed portion adjacent the planar portion, and the fluid coupling conduit further comprises:
   a flapper component disposed on the body, wherein the flapper component is structured to move between an open position and a closed position, in the open position the flapper component engages the recessed portion, and the flapper component moves away from the recessed portion when moving from the open position to the closed position.

13. The patient interface device of claim 8, wherein the blocking member is coupled to the body by a snap-fit mechanism.

14. The patient interface device of claim 8, wherein the middle portion of the body has an atmospheric port disposed opposite and distal from the relief aperture.

* * * * *